US006815948B1

United States Patent
Kwun et al.

(10) Patent No.: US 6,815,948 B1
(45) Date of Patent: Nov. 9, 2004

(54) METHOD OF DETECTING TENSION WIRE BREAK IN CONCRETE POLE

(75) Inventors: Hegeon Kwun, san Antonio, TX (US); Sang-Young Kim, San Antonio, TX (US); Kyoichi Asano, Tokyo (JP)

(73) Assignee: The Tokyo Electric Power Company, Inc., Tokyo (JP)

( * ) Notice: Subject to any disclaimer, the term of this patent is extended or adjusted under 35 U.S.C. 154(b) by 0 days.

(21) Appl. No.: 10/673,649

(22) Filed: Sep. 30, 2003

(51) Int. Cl.[7] .............................................. G01N 27/82
(52) U.S. Cl. ..................................................... 324/238
(58) Field of Search ................................ 324/219–220, 324/228, 232, 234, 238, 239–240; 73/584, 596–598

(56) References Cited

U.S. PATENT DOCUMENTS 6,205,859 B1 * 3/2001 Kwun et al. .................. 73/579
6,624,628 B1 * 9/2003 Kim et al. ................... 324/240

* cited by examiner

*Primary Examiner*—Bot LeDynh
(74) *Attorney, Agent, or Firm*—Westerman, Hattori, Daniels & Adrian, LLP

(57) ABSTRACT

A method and apparatus for the nondestructive detecting of tension wires in a concrete pole from a single test location without requiring scanning along the length of the pole and without requiring direct contact to the wires. The method and apparatus utilize longitudinal guided waves in tension wires that are generated and detected based on the magnetostrictive sensor principle. The detected signals from broken tension wires and from the ends of concrete pole are analyzed for the number and locations of broken wires.

13 Claims, 6 Drawing Sheets

METHOD OF DETECTING TENSION WIRE BREAK IN CONCRETE POLE

BACKGROUND OF THE INVENTION

1. Field of the Invention

The present invention relates to a method of detecting a tension wire break in a concrete pole.

2. Description of the Related Art

Generally, concrete poles are widely used for supporting power distribution lines and other electric wires such as, for example, communication lines provided by Nippon Telegraph and Telephone Corporation (NNT), etc. and overhead contact lines for railroads and used for installing lighting systems, traffic signals, golf nets, antennas, and the like. This invention is particularly suitable for testing of concrete electric poles. Concrete electric poles are widely used for electric power distribution lines in numerous countries. The poles are generally 14 to 15 meters in height and are made in the shape of a tapered cylinder with an approximately 50-mm thick concrete wall. The outside diameter of the pole is typically about 20 cm at the top end, the diameter increasing to about 40 cm at the bottom end. In the middle of the concrete wall, the pole typically contains 12 to 20 tension wires that are arranged around the circumference with equal angular spacing and run longitudinally along the entire length of the pole. Additionally, the concrete wall of the pole contains a number of rebar that are placed between tension wires and run longitudinally from the bottom end of the pole but not through the entire length. Typical diameters of the tension wires and rebar are 7 nun. The tension wires are prestressed during concrete casting and curing to supply the bending strength to the concrete pole needed to withstand up to hurricane-force winds.

During the long service life of a concrete electric pole, stress corrosion cracking (SCC) can develop in the tension wires due to water seeping through cracks in the concrete wall and becoming tapped around the wires. The SCC generally produces a tight fracture in tension wire. When a pole contains broken tension wires, its bending strength is significantly weakened and, unless replaced or strengthened, it could suddenly fail under gusty winds that may result in serious accidents. To ensure the structural integrity and safety of a pole, the aging concrete poles need to be inspected for the presence of broken tension wires using a suitable nondestructive evaluation (NDE) method.

As shown in FIGS. 1 and 2, in order to obtain a deflective strength necessary to resist a bending moment, a concrete pole has a "prestressed" structure for imparting a compressive stress to a concrete, in which a high-strength wire such as a piano wire is cast in a mold in a tensioned manner. FIG. 1 shows load imposed on supporting structure, including wind load 1, tensile load 2 and compressive load 3. FIG. 2 shows cross sections of a typical concrete pole at two levels, at 8 meters in height 7 and at 2.4 meters 8. Inside the pole are tension wires 4 and non-tension wires 5. If a tension wire is broken due to corrosion or the like, the concrete pole becomes reduced in deflective strength, which may lead to a breakage accident. Thus, a technique for nondestructive detection of a wire break is desired.

Even if the tension wire which is a high-tension steel is broken due to stress-corrosion cracking, the wire excluding a broken portion is held by the concrete without displacement, and also protected by an alkali contained in the concrete to thereby exhibiting no sectional phenomenon. The broken portion has only a slight gap, and is therefore not easily detected.

The break of the tension wire can be detected by means of radiography. However, in order to discover a wire break that cannot be specified as to where the break occurs in the concrete pole having a length of extending up to tens of meters, many radiographs are needed because a coverage per radiograph is limited. In addition, a site where the radiography is performed must be set up as a controlled area, so that it is substantially impossible to perform the radiography in an urban area.

Eddy current testing (ECT) or ultrasonic testing (UT) can also be used to detect conditions of the wire inside the concrete pole. However, the gap between broken ends of a wire is small, and the inspection is necessarily performed through concrete having a thickness of approximately 25 mm, thereby making it difficult to detect a wire break. Further, in both ECT and UT, a probe needs to be moved while being in close contact with the outer surface of the pole. However, this operation is difficult due to obstacles such as attached hardware and metal bands. Even in the case without obstacles, the probe is moved slowly in a longitudinal direction of the pole, thereby requiring much time for the inspection.

SUMMARY OF THE INVENTION

In view of the above, an object of the present invention is to make it possible to detect tension wire breaks in a concrete pole in a short period of time without scanning along the entire concrete pole with a detection device.

To achieve the above-mentioned object, a pulse of relatively low frequency (typically about 10 to 20 kHz) mechanical wave called a guided wave is generated in a wire, and propagated in its longitudinal direction, and signals reflected from the ends of the concrete pole and broken wires are detected. The signal reflected from a broken wire occurs earlier than the end-reflected signal. The presence, and the lengthwise position, of broken wires are determined from the signals occurring before the end signal and their arrival time. Among methods of generating a guided wave, a method using magnetostrictive sensors (MsS) (hereinafter, referred to as "MsS method") proposed by researchers at Southwest Research Institute (SwRI), makes it possible that a guided wave pulse is excited in a wire in a noncontact manner through magnetic coupling, and also that a reflected pulse is detected in a noncontact manner. U.S. Pat. Nos. 5,456,113, 5,457,994, 5,581,037, and 5,767,766 describe the MsS method, and are incorporated herein by reference.

The present invention is a special application of the above MsS methods modified for concrete pole tension wire inspections. While such testing of exposed wires has been previously effected, such testing of wires embedded in concrete has not only not been effected, but was previously thought impossible.

FIG. 3 shows a bias magnetic field coil for generating a static magnetic field in a longitudinal direction using a DC current and a probe coil installed to the vicinity of a top end (portion having only tension wires without rebars) of a concrete pole. FIG. 4 shows a system unit for driving the probe coil, a personal computer with keyboard for collecting data, and a bias magnetic field coil power supply.

If an AC pulse is applied to the probe coil, the magnetic field in the axial direction is changed, and a wave of condensation and rarefaction is generated in the axial direction of the wire due to a magnetostrictive effect to be propagated as the guided wave. In the case without a broken wire, a signal reflected only from an end portion of the concrete pole is detected, and in the case where the wire is broken, a signal reflected from a position where the wire is broken is detected. Generally, 12 to 20 tension wires are embedded inside a concrete pole, and if multiple wires are broken at the same position in the longitudinal direction, a reflected signal having a strength corresponding to the number of broken wires would be obtained. If many numbers of wires are broken, a signal reflected from the end portion would be weaker. If most of the wires are broken, the signal reflection at the end portion would substantially disappear. Accordingly, the level of the wire break could be determined based on the broken-wire signals and decrease in the end-reflected signals.

According to the method of the present invention, from a single test location on a concrete pole without requiring scanning along the length of the pole and without direct contact to the tension wires, wire breaks in all the tension wires in the concrete pole are simultaneously examined. in a short period of time. The above approach examines all tension wires simultaneously. Therefore, when broken wire signals are detected, which individual wires among them are broken can not be identified from the data. Individual broken wires could be identified by using the encircling coil probe in FIG. 3 as the transmitter of the guided waves and a U-shaped probe illustrated in FIG. 6 as a separate receiver that is scanned around the circumference of the pole for the maximum broken wire signal.

DETAILED DESCRIPTION OF THE INVENTION

The inventive apparatus and method are now described. The first step involves installing the MsS and DC bias electromagnetic (EM) coils around a concrete pole at an appropriate location and height above the top ends of rebars so that guided waves are generated only in tension wires and not in rebars.

When an AC pulse is applied to the probe coil, the magnetic field in the axial direction is changed, and a wave of condensation and rarefaction is generated in the axial direction of the wire due to a magnetostrictive effect to be propagated as the guided wave. In the case without a broken wire, a signal reflected only from an end portion of the concrete pole is detected, and in the case where the wire is broken, a signal reflected from a position where the wire is broken is detected. Generally, 12 to 20 tension wires are embedded inside a concrete pole, and if a plurality of wires are broken at the same position in the longitudinal direction, a reflected signal having a strength corresponding to the number of broken wires would be obtained. If many numbers of wires are broken, a signal reflected from the end portion would be weaker. If most of the wires are broken, the signal reflection at the end portion would substantially disappear. Accordingly, the level of the wire break could be determined based on the broken-wire signals and decrease in the end-reflected signals.

Figure 1:
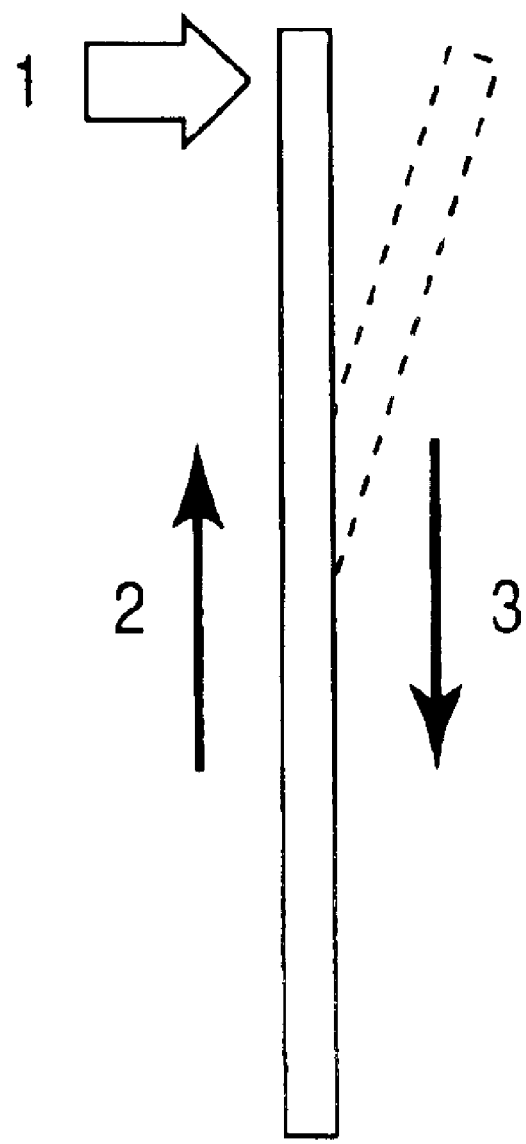
FIG. 1 a diagram of a concrete electrical pole.
Figure 2:
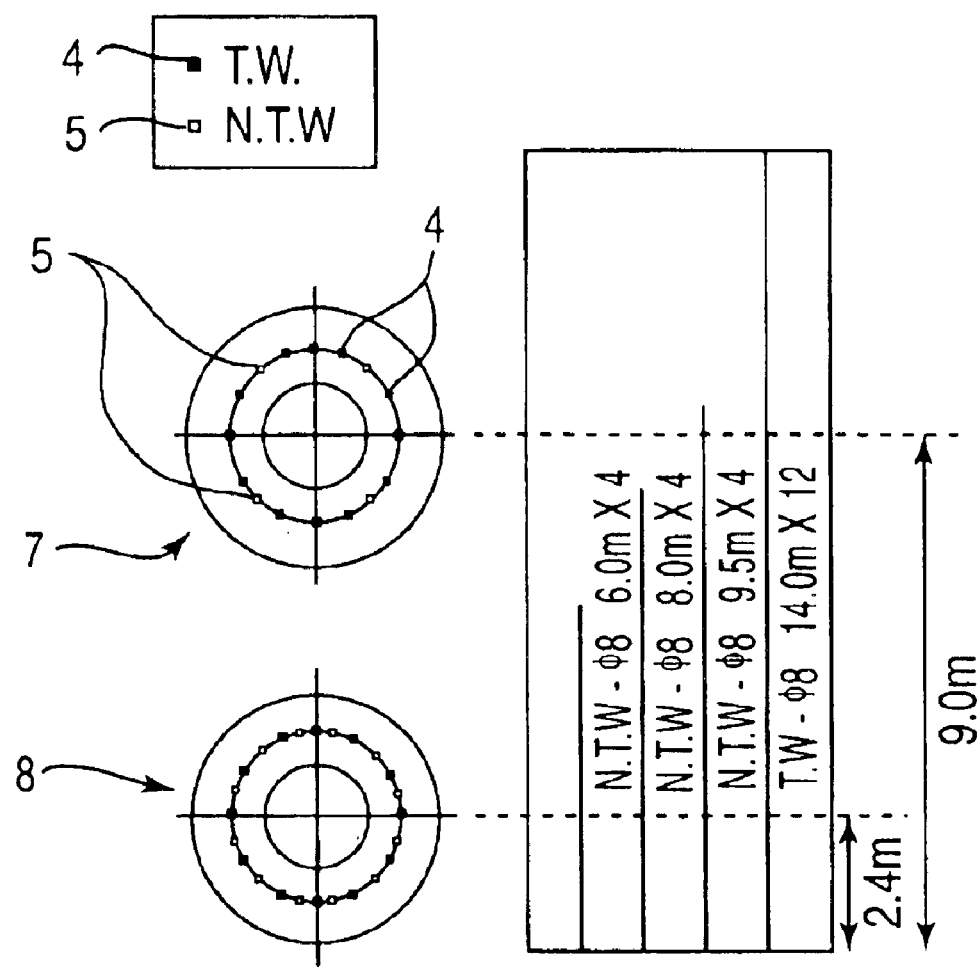
FIG. 2 shows a schematic of the interior of a concrete electric pole.
Figure 3:
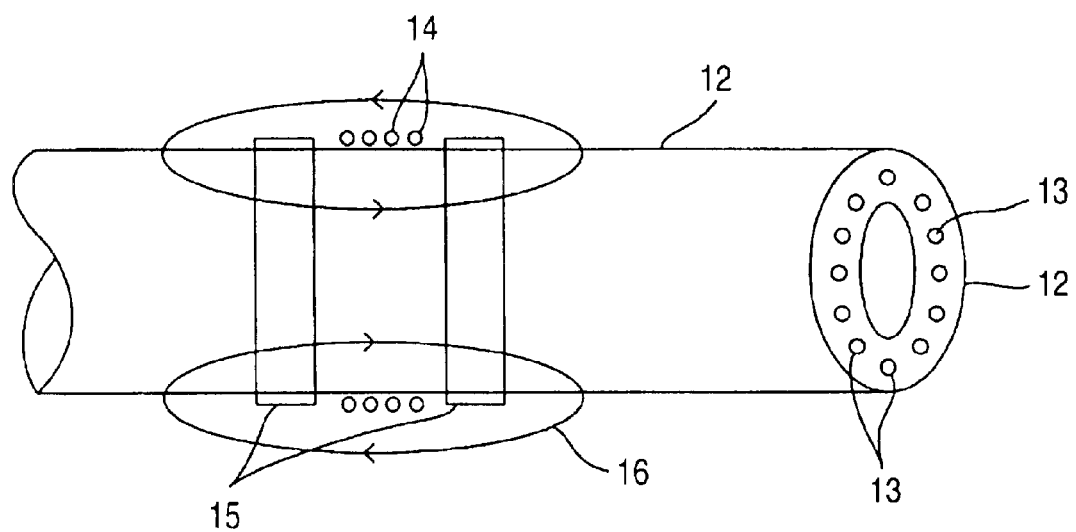
FIG. 3 shows a bias magnetic field coil and a probe coil installed on the top end of a concrete pole.
Figure 4:
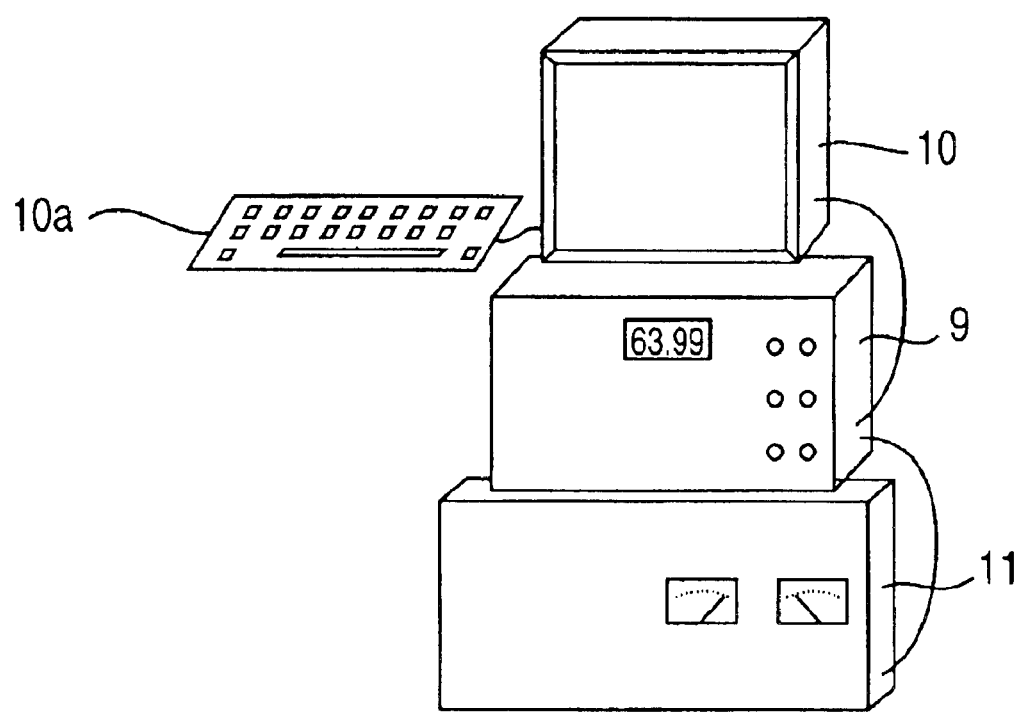
FIG. 4 shows a system unit, a personal computer, and a bias magnetic field coil power supply for the apparatus of FIG. 3.

FIG. 3 shows MsS coils 14 and DC bias EM coils 15 that are installed on a concrete pole 12 having tension wires 13 contained therein. The MsS coils 14 are supplied with a high-frequency pulse for generating a guided wave from a system unit 9 shown in FIG. 4 via a cable (not shown). FIG. 4 shows a system unit 9, a personal computer 10 for controlling the system unit 9 and for collecting, storing, and analyzing data, and a bias magnetic field coil power supply 11. Referring back to FIG. 3, the MsS coils 14 also detect the reflected signals, which are then amplified, filtered, recorded, and displayed in the system units 9 and 10.

The DC bias EM coils 15 are supplied with a DC current from a bias magnetic field coil power supply 11 via a cable (not shown). When sufficient DC electric current is applied to the EM coils 15, a suitable level of DC bias magnetic field 16 needed for generation and detection of longitudinal (L) mode guided waves is established in the tension wires 13. Utilizing the direction control function in the system 9, guided waves are then launched along the tension wires 13 toward the bottom end of the concrete pole 12 and signals are reflected back from the ends of broken wires and from the bottom end of the pole and detected by the MsS coils 14 and subsequently by the system unit 9. In a subsequent action, guided waves are launched along the tension wires toward the top of the pole 12. Signals are reflected back from the ends of broken wires and from the top end of the pole and detected by the MsS coils 14 and subsequently by the system unit 9.

The signals received by the system unit are analyzed for the presence of broken tension wires, including their numbers and locations along the pole length.

Figure 5:
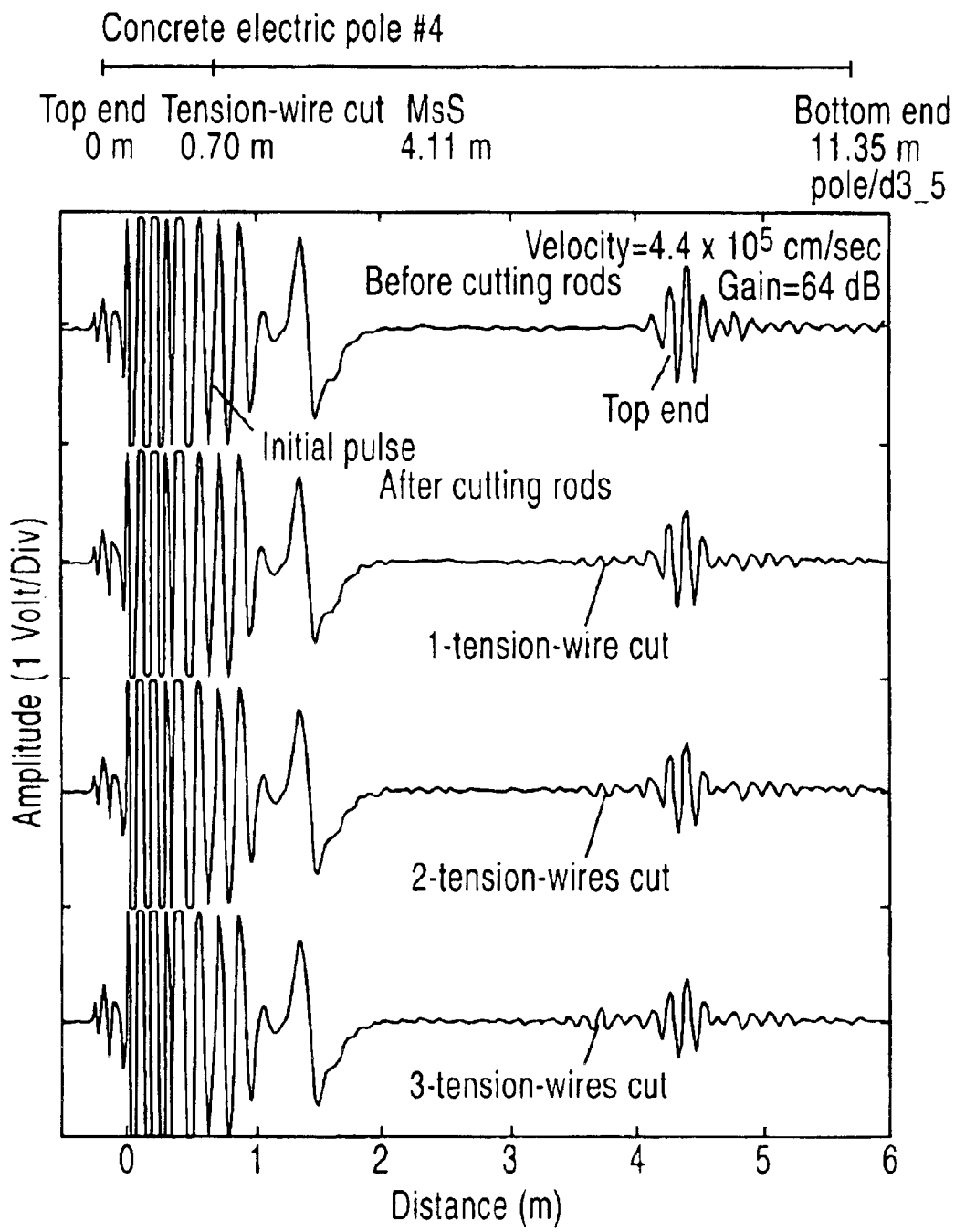
FIG. 5 shows a graph of data collected during testing of a concrete pole.

FIG. 5 shows data that were obtained during testing of a concrete pole when 3 tension wires are cut one by one for a concrete pole having no broken tension wire. It is observed that a signal at a cut portion 3.4 m forward from a probe setting position (0 of the abscissa) becomes stronger as the number of cut wires grows. Simultaneously, it is also observed that a signal at an end portion (top end) 4.1 m forward from the probe setting position becomes weaker as the number of cut wires grows.

As illustrated in FIG. 5, the MsS coils were installed at an approximately 4.11 meter distance from the top end of the pole and a 20 kHz L-mode guided waves were launched toward the top end of the pole. The data were then acquired before and after placing cuts in the tension wires approximately 0.7 meters from the top end of the pole. The data demonstrate that (1) guided waves can be generated and detected in the tension wires using the invented method and apparatus and (2) that inspection of entire concrete poles for broken tension wires can be achieved from a single test location. The data also show that (1) a 1-tension wire cut produced detectable signals, (2) if multiple wires were cut at the same axial location along the pole, the wire-cut signal increased its amplitude, and (3) the signal reflected from the end decreased in amplitude with an increasing number of wires cut.

As can be seen in FIG. 5, the presence of broken wires is determined by detecting either individual broken wire signals, or the decrease in the end reflected signal amplitude, or both. Individual broke wire signals are used to determine the number of broken wires and their axial locations along the pole length. With suitable calibration, the end-reflected signal is used to determine the total number of broken wires in pole, but not their axial locations. Because the data show signals from all tension wires in the pole simultaneously, angular positions of the broken wires around the pole circumference can not be determined from the data.

Figure 6:
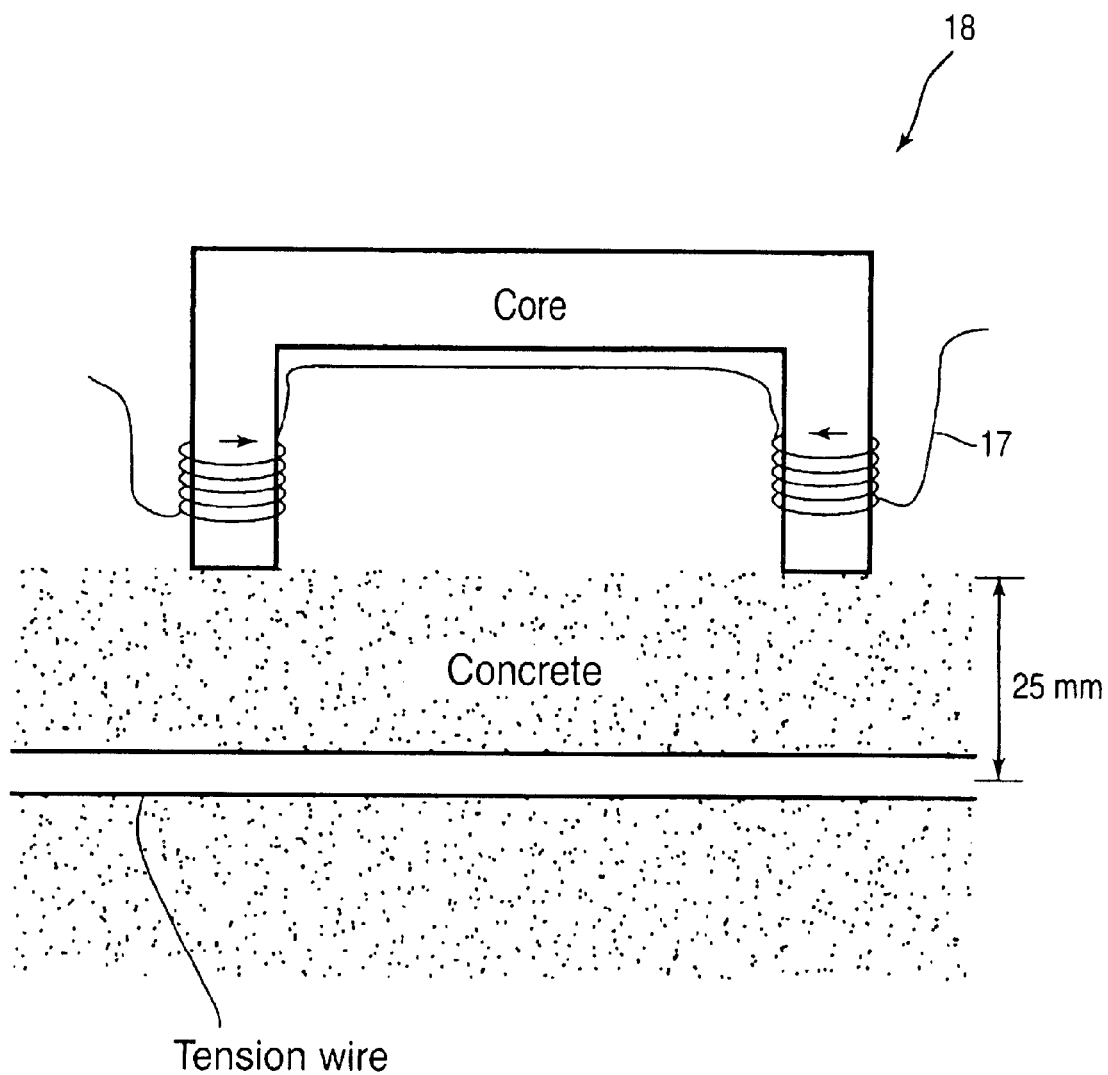
FIG. 6 shows an apparatus of the present invention for testing of an individual tension wire.

In addition to the simultaneous inspection of all tension wires in a concrete pole, the condition of individual tension wires can also be determined by using a U-shaped MsS probe illustrated in FIG. 6 as the signal detector. The MsS probe consists of a U-shaped core 18 (typically made of ferrite) with coils 17 wound around the two legs of the core in opposite direction to minimize the common-mode electromagnetic noise (described in U.S. Pat. No. 5,767,766). The angular position of an individual tension wire is determined by adjusting the circumferential location of the MsS probe until a detected guided wave signal is maximized. The inspection of individual tension wires using the U-shaped MsS probe is more time-consuming but provides more detailed information than the simultaneous inspection of all tension wires using the encircling MsS coils. Also, the U-shaped MsS probe inspection is expected to be superior than the counterpart for detecting individual broken wires because a single broken wire signal detected using the encircling MsS coils is relatively small compared to the background noise level and, therefore, may not be reliably detectable due to an insufficient signal-to-noise ratio.

It will be appreciated that variations and modifications will become apparent to persons skilled in the art. Such variations and modifications should be considered to fall within the spirit and scope of the invention as broadly described hereinbefore and as claimed hereinafter.

We claim:

1. A method for the nondestructive evaluation of tension wires embedded in a concrete pole, comprising the steps of:
   establishing a DC magnetic field needed for MsS operation on the concrete pole;
   applying a pulse of AC magnetic field that generates a guided wave in the tension wires based on the magnetostrictive effect;
   detecting the guided wave signals reflected from the ends of the tension wires and the ends of the concrete pole based on the inverse magnetostrictive effect;
   analyzing and correlating the detected signal with patterns of changes known to be indicative of a break or breaks in the tension wires; wherein the above steps are effected without physically contacting the tension wires, and wherein said steps of establishing a DC magnetic field, applying a pulse of AC magnetic field, and detecting the guided wave signals are each effected from a single location on the pole.

2. The method of claim 1, wherein said step of establishing a DC magnetic field comprises positioning a permanent or electromagnetic bias magnet on the concrete pole at a location where no rebars are present in a sectional plane of the concrete that is perpendicular to the longitudinal direction of the pole.

3. The method of claim 1, wherein said step of applying a pulse of AC magnetic field comprises the step of encircling the concrete pole with MsS coils at the location where the DC magnetic field has been established, and then applying a pulse of electric current of suitable frequency through the coil so as to generate the guided waves in the tension wires based on the magnetostrictive effects.

4. The method of claim 3 wherein said step of detecting the guided wave signals reflected from the tension wires and ends of the concrete pole is effected by using the MsS coils and analyzing the detected signals for broken wires.

5. A method for the nondestructive evaluation of tension wires embedded in a concrete pole, comprising the steps of:
   establishing a DC magnetic field needed for MsS operation on the concrete pole;
   applying a pulse of AC magnetic field to simultaneously generate a guided wave simultaneously in the tension wires based on the magnetostrictive effect;
   detecting the guided wave signals reflected from the ends of the tension wires and the ends of the concrete pole based on the inverse magnetostrictive effect;
   analyzing and correlating the detected signals with patterns of changes known to be indicative of a break in some or all of the tension wires;
wherein the above steps are effected without physically contacting the tension wires, and
wherein said steps of establishing a DC magnetic field, applying a pulse of AC magnetic field, and detecting the guided wave signals are each effected from a single location on the pole.

6. The method of claim 5, wherein said step of establishing a DC magnetic field comprises positioning a permanent or electromagnetic bias magnet proximate to the tension wires.

7. The method of claim 5, wherein said step of applying a pulse of AC magnetic field comprises the step of placing an electromagnetic coil proximate to the tension wires, and then varying an electric current through the electromagnetic coil so as to produce magnetostrictive effects within the tension wires.

8. The method of claim 5, wherein said step of detecting the guided wave signals comprises the step of placing an electromagnetic pickup coil proximate to the tension wires, and detecting variations in a voltage induced in the electromagnetic coil caused by an inverse magnetostrictive effect within the tension wires.

9. A method for the nondestructive evaluation of a tension wire embedded in a concrete pole, comprising the steps of:
   establishing a DC magnetic field needed for MsS operation on the concrete pole;
   applying a pulse of AC magnetic field that generates a guided wave in the tension wire based on the magnetostrictive effect;
   detecting the guided wave signal reflected from the end of the tension wire and the ends of the pole based on the inverse magnetostrictive effect;
   analyzing and correlating the detected signal with patterns of changes known to be indicative of a break in the tension wire;
wherein the above steps are effected without physically contacting the tension wire, and
wherein said steps of establishing a DC magnetic field, applying a pulse of AC magnetic field, and detecting the guided wave signal are each effected from a single location on the pole.

10. The method of claim 9, wherein said step of establishing a DC magnetic field comprises positioning a permanent or electromagnetic bias magnet proximate to the tension wire.

11. The method of claim 9, wherein said step of applying a pulse of AC magnetic field comprises the step of placing an electromagnetic coil proximate to the tension wire, and then varying an electric current through the electromagnetic coil so as to produce magnetostrictive effects within the tension wire.

12. The method of claim 9, wherein said step of detecting the guided wave signal comprises the step of placing an electromagnetic pickup coil proximate to the tension wire, and detecting variations in a voltage induced in the electromagnetic coil caused by an inverse magnetostrictive effect within the tension wire.

13. The method of claim 12, wherein the electromagnetic pickup coil is a U-shaped MsS probe.

* * * * *